US00PP26473P3

(12) United States Plant Patent
Madsen

(10) Patent No.: US PP26,473 P3
(45) Date of Patent: Mar. 8, 2016

(54) ***RHIPSALIDOPSIS* PLANT NAMED 'PKMRHIPS09'**

(50) Latin Name: ***Rhipsalidopsis* Britton et Rose**
Varietal Denomination: PKMRhips09

(71) Applicant: Gartneriet PKM A/S, Odense N (DK)

(72) Inventor: Christian Hald Madsen, Korsør (DK)

(73) Assignee: GARTNERIET PKM A/S, Odense N (DK)

( * ) Notice: Subject to any disclaimer, the term of this patent is extended or adjusted under 35 U.S.C. 154(b) by 121 days.

(21) Appl. No.: 13/999,833

(22) Filed: Mar. 27, 2014

(65) Prior Publication Data

US 2015/0282411 P1 Oct. 1, 2015

(51) Int. Cl.
*A01H 5/00* (2006.01)

(52) U.S. Cl.
USPC ..... Plt./372

(58) Field of Classification Search
USPC ..... Plt./372
See application file for complete search history.

*Primary Examiner* — Annette Para
(74) *Attorney, Agent, or Firm* — Foley & Lardner LLP

(57) ABSTRACT

A new and distinct *Rhipsalidopsis* plant named 'PKMRhips09' particularly characterized by its compact plant habit; dense and bushy plant form; moderate growth rate; and orange-red colored buds and flowers.

5 Drawing Sheets

Latin name of the genus and species of the plant claimed: *Rhipsalidopsis* Britton et Rose.

Variety denomination: 'PKMRhips09'.

BACKGROUND OF THE INVENTION

The present invention relates to a new and distinct cultivar of *Rhipsalidopsis*, botanically known as *Rhipsalidopsis*, sometimes referred to as *Rhipsalidopsis* Britton et Rose, including *Epiphylopsis* Berger, commonly known as either Easter Cactus or Spring Cactus, and hereinafter referred to by the cultivar name 'PKMRhips09'.

The new *Rhipsalidopsis* cultivar is a product of a controlled breeding program conducted by the inventor, Christian Hald Madsen, in Søhus, Denmark.

The new *Rhipsalidopsis* cultivar originated from a cross made by the inventor in 2007 in Søhus, Denmark. The female and male parents are unpatented, proprietary *Rhipsalidopsis*× *hybrida* cultivars. The new *Rhipsalidopsis* cultivar was discovered and selected by the inventor as a single flowering plant within the progeny of the stated cross in a controlled environment in 2010 in Søhus, Denmark. The inventor selected 'PKMRhips09' on the basis of its flower color and compact, freely branching, upright growth habit.

Asexual reproduction of the new *Rhipsalidopsis* cultivar by phylloclade cuttings was first performed in 2008 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMRhips09' which distinguish this *Rhipsalidopsis* as a new and distinct cultivar:

1. Upright growth habit and upright flowers;
2. Moderately vigorous growth; and
3. Orange-red colored buds and flowers.

Data and plants of the parent cultivars are no longer available for comparison with the claimed cultivar.

The most similar commercial cultivar to the instant cultivar 'PKMRhips09' is the *Rhipsalidopsis* cultivar 'PKMrh02' (Patented, U.S. Plant Pat. No. 21,425). Plants of the instant cultivar 'PKMRhips09' differ primarily from plants of *Rhipsalidopsis* 'PKMrh02' in the following characteristics:

1. Plants of 'PKMRhips09' have shorter phylloclades than plants of 'PKMrh02' and are thus lower overall in total height;
2. Plants of 'PKMRhips09' have more red colored flower buds and flowers than plants of 'PKMrh02';
3. Plants of 'PKMRhips09' have white filaments whereas plants of 'PKMrh02' have purple filaments;
4. Plants of 'PKMRhips09' do not have purple phylloclade margins while plants of 'PKMrh02' have purple phylloclade margins; and
5. Plants of 'PKMRhips09' have less dark purple ovaries than plants of 'PKMrh02'.

BRIEF DESCRIPTION OF THE PHOTOGRAPHS

The accompanying photographs illustrate the overall appearance of the new *Rhipsalidopsis* cultivar 'PKMRhips09' showing the colors as true as is reasonably possible with colored reproductions of this type. Colors in the photographs may differ slightly from the color values cited in the detailed botanical description, which accurately describe the color of 'PKMRhips09'.

DETAILED BOTANICAL DESCRIPTION

Figure 1:
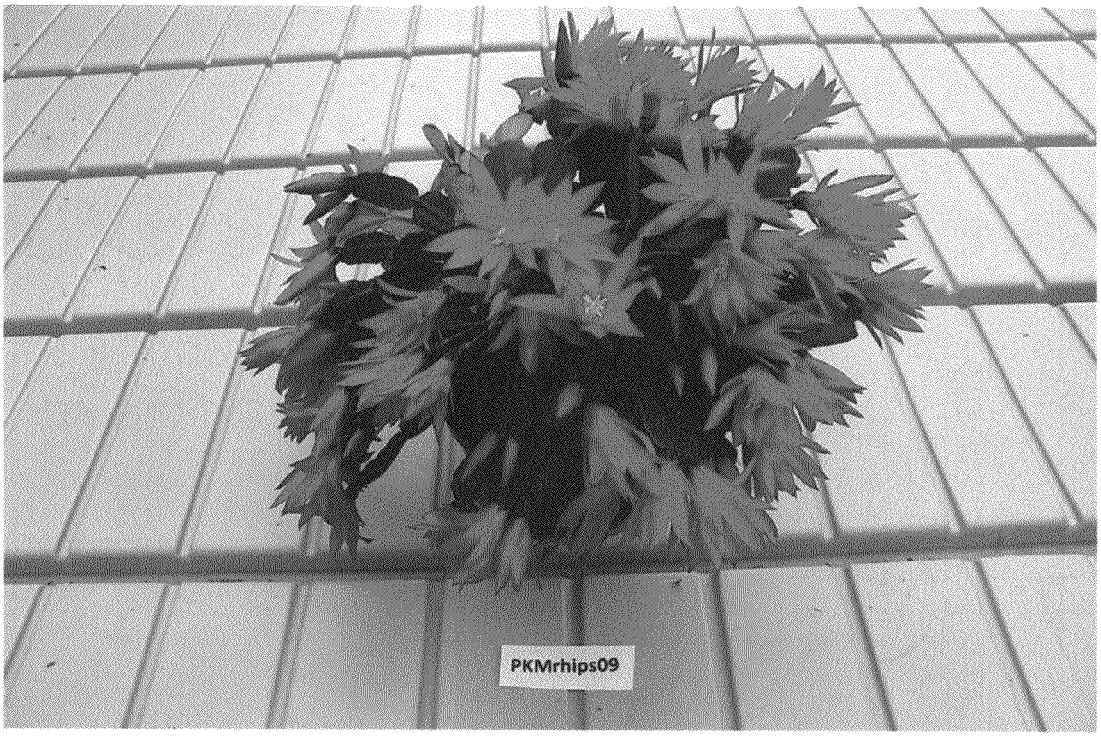
FIG. 1 shows a typical flowering plant of 'PKMRhips09' grown in a 10.5 cm pot.
Figure 2:
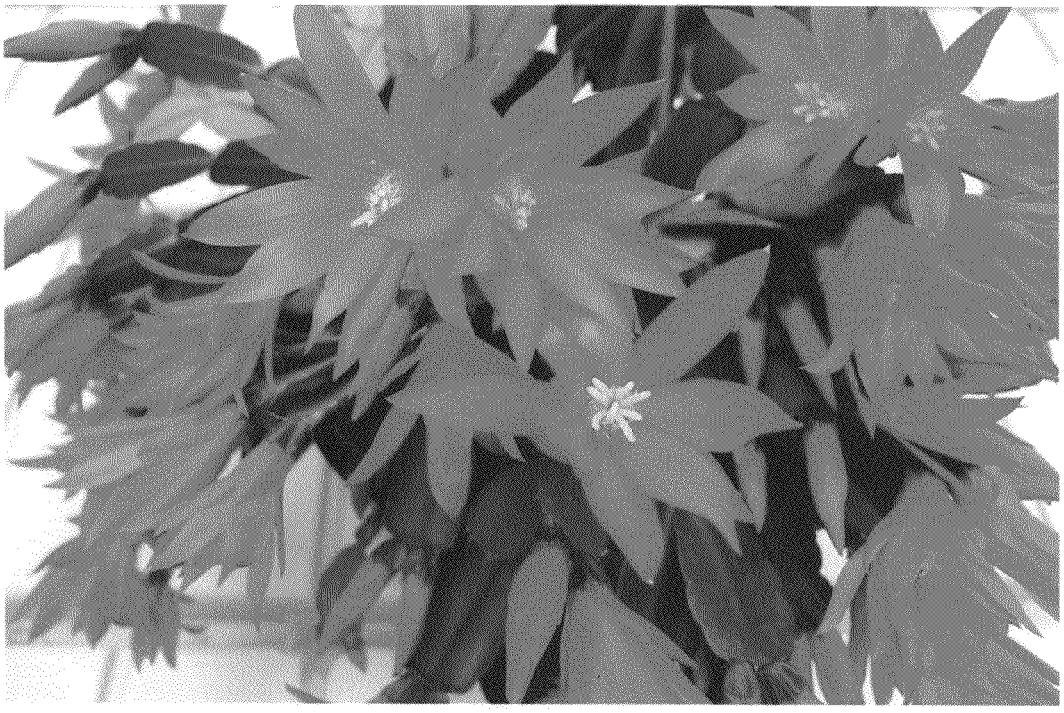
FIG. 2 shows a close-up view of typical buds, flowers, and phylloclades of 'PKMRhips09'.
Figure 3:
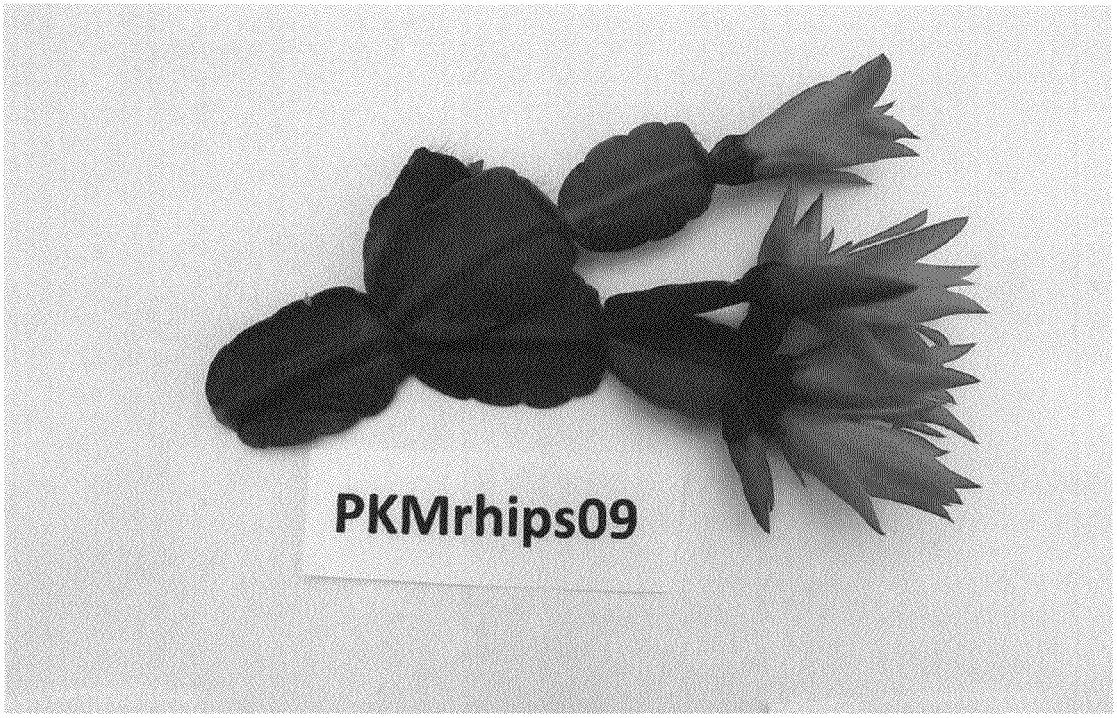
FIG. 3 shows a typical lateral branch, with phylloclades, buds, and flowers of 'PKMRhips09'.
Figure 4:
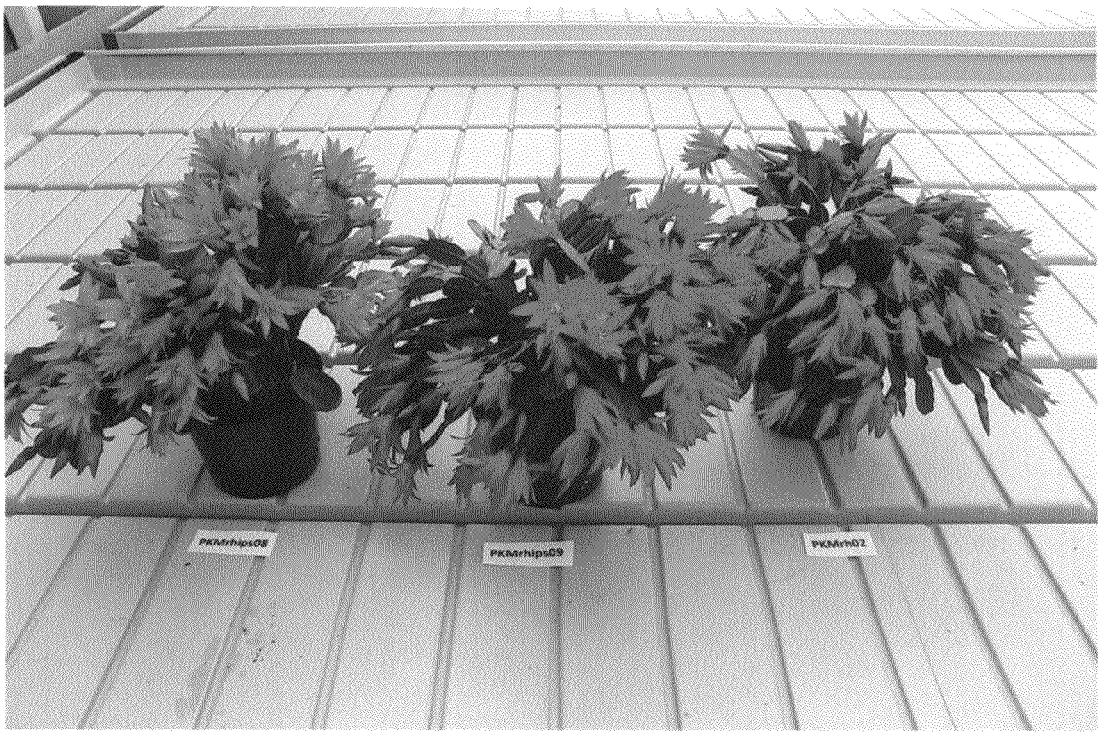
FIG. 4 shows a comparison of a typical plant of 'PKMRhips09' (center) with a typical plant of a similar variety 'PKMRhips08' (left) and a typical plant of the comparison variety 'PKMRh02' (right).
Figure 5:
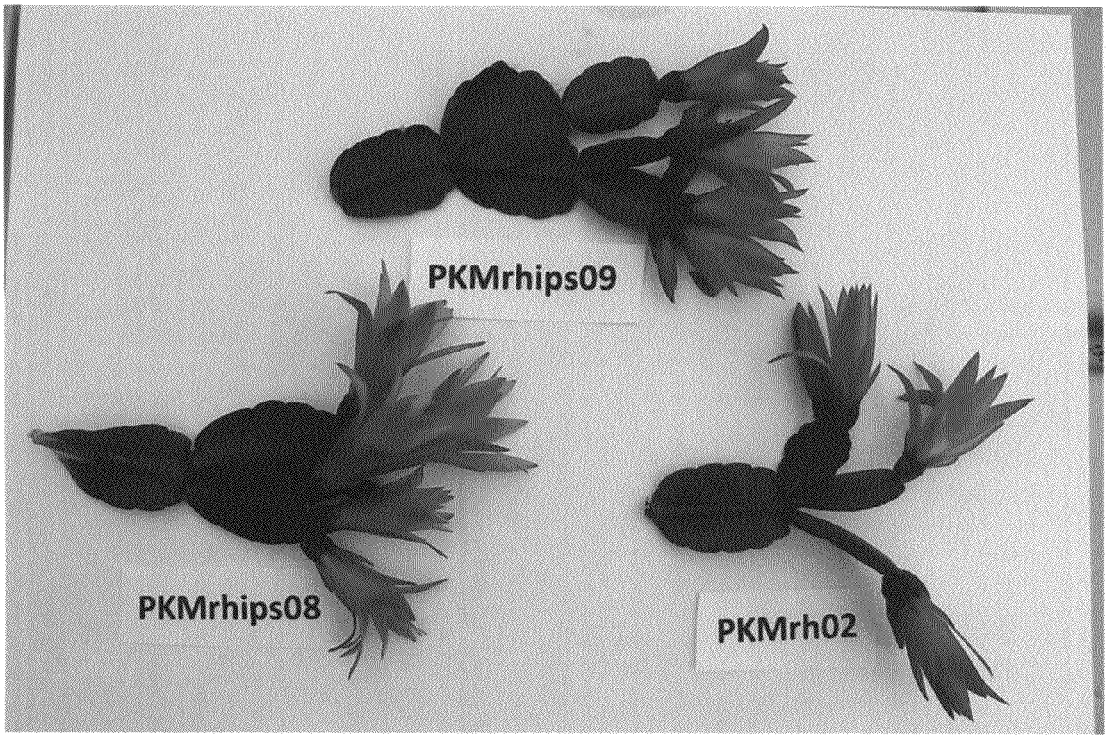
FIG. 5 shows a comparison of typical laterals branches, with phylloclades, buds, and flowers, of the varieties 'PKMRhips09', 'PKMRhips08', and 'PKMrh02'.

The new *Rhipsalidopsis* cultivar 'PKMRhips09' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMRhips09' as grown in a glass-covered greenhouse in Fyn, Denmark, under conditions which closely approximate those generally used in commercial practice, where day temperatures in the greenhouse average 18° C. and night temperatures in the greenhouse average 16° C. Ambient light levels used while growing plants of 'PKMRhips09' are +50 $Wm^2$. No growth retardants were used when growing plants of 'PKMRhips09'.

The age of the 'PKMRhips09' plants described is about 10-12 months after propagation and grown in 10.5 cm pots. The photographs and descriptions were taken during the winter season. Color references are made to The Royal Horticultural Society Colour Chart (R.H.S.), $5^{th}$ edition, except where general colors of ordinary significance are used.

Classification:

*Botanical.*—*Rhipsalidopsis* Britton et Rose.

*Common name.*—Easter Cactus or Spring Cactus.

*Variety denomination.*—PKMRhips09.

Parentage:

*Female or seed parent.*—Unpatented, proprietary *Rhipsalidopsis* Britton et Rose cultivar.

*Male or pollen parent.*—Unpatented, proprietary *Rhipsalidopsis* Britton et Rose cultivar.

Propagation: By phylloclade cuttings.

*Time and temperature to initiate roots.*—In a greenhouse, about 2 months at 18° C. to 21° C.

*Rooting habit and description.*—Fine, well-branched.

Plant:

*Type.*—Perennial, Epiphyte.

*Overall shape.*—Upright.

*Form.*—Dense and Bushy.

*Growth habit.*—Branched.

*Branching habit.*—1-4 new phylloclades forming at the apical end of older phylloclades. No pinching required.

*Growth rate.*—Moderate.

*Vigor.*—Good.

*Crop time.*—About 10-12 months are required to produce a finished flowering plant.

*Size at maturity.*—Height (soil level to top of plant, excluding flowers): About 13-15 cm. Spread: About 25-30 cm, excluding flowers.

Stem: None, older phylloclades may turn woody with age (several years).

Phylloclade:

*Arrangement.*—Phylloclades form at the apex of older phylloclades to form branches.

*Aspect.*—Upright to arching (from basal phylloclade).

*Strength.*—Strong (from basal phylloclade).

*Length.*—About 25-35 mm.

*Width.*—Up to 24 mm.

*Overall shape.*—Oval.

*Apex shape.*—Truncate.

*Base shape.*—Rounded.

*Margin.*—Crenate.

*Texture.*—Glabrous, smooth.

*Pubescence.*—Approx. 1-5 hairs up to 4 mm long at areoles along margins.

*Color of mature phylloclade.*—Upper and lower surfaces: RHS 146A, yellow-green.

*Venation.*—None.

Flower description:

*Natural flowering season.*—Flowering occurs from February to April (northern hemisphere), but can be changed by cold treatment. Flowers persistent, sessile.

*Flowering response time.*—About 8 to 9 weeks after end of cold treatment.

*Flowering longevity* (*dependent on temperature and light conditions*).—About 5 to 6 days.

*Fragrance.*—None.

*Quantity of flowers per terminal phylloclade.*—About 1 to 4.

*Quantity of flowers and buds per plant.*—Over 100.

*Flower bud.*—Length: Ranging from 0 to 40 mm (before anthesis). Width: Ranging from 0 to 10 mm. Shape: Ovoid to lanceolatoid. Color: RHS 34A, Orange-red.

*Flower.*—Shape: Actinomorphic. Aspect: Upright to vertical during development. Persistent or self-cleaning: Persistent. Height: Up to 4 cm (including ovary). Diameter: Up to 7 cm.

*Tepals.*—Arrangement: Actinomorphic; not fused. Quantity: 15-20. Length: Up to 35 mm. Width: Up to 7 mm. Shape: Broad oblanceolate. Apex: Acute. Margin: Entire. Texture: Smooth and Silky. Color, upper and lower surfaces: RHS 34A, Orange-red. Color does not fade.

Reproductive organs:

*Androecium.*—Stamen: Quantity: Many (>100). Anther: Shape: Oblong. Length: About 1 mm. Color: RHS 14B, yellow-orange. Filament: Length: 15 mm. Color: Between RHS N155C and N155D, White. Pollen: Amount: Plenty. Color: RHS 14B, yellow-orange.

*Gynoecium.*—Pistil: Quantity: 1. Stigma: Shape: Branched. Color: Between RHS 155A and RHS 155B, white. Style: Length: 15 mm. Color: Base: white. Middle: Orange. Apex: Orange-Red. Style is too small to determine R.H.S. value. Ovary: Color: yellow-green with purple ridges. Areas of different colors too small to determine R.H.S. values.

Seeds/fruit: None observed.

Disease/pest resistance and susceptibility: Not tested.

Temperature tolerance: Tolerant to a low temperature of about 2° C. and to a high temperature about 40° C.

I claim:

1. A new and distinct *Rhipsalidopsis* plant named 'PKMRhips09', as illustrated and described herein.

* * * * *